(12) United States Patent
Nakai et al.

(10) Patent No.: US 7,989,492 B2
(45) Date of Patent: Aug. 2, 2011

(54) EPIGALLOCATECHIN DIMERS OR TRIMERS HAVING LIPASE INHIBITORY ACTIVITY AND/OR ANTIOXIDANT ACTIVITY

(75) Inventors: Masaaki Nakai, Minoo (JP); Yuko Fukui, Takatsuki (JP); Sumio Asami, Ibaraki (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 616 days.

(21) Appl. No.: 11/597,291

(22) PCT Filed: May 26, 2005

(86) PCT No.: PCT/JP2005/009666
§ 371 (c)(1),
(2), (4) Date: Apr. 28, 2008

(87) PCT Pub. No.: WO2005/116005
PCT Pub. Date: Dec. 8, 2005

(65) Prior Publication Data
US 2008/0275258 A1 Nov. 6, 2008

(30) Foreign Application Priority Data
May 27, 2004 (JP) .................................. 2004-158463

(51) Int. Cl.
*A61K 31/353* (2006.01)
(52) U.S. Cl. ........................................ 514/456; 426/597
(58) Field of Classification Search .................. 514/456
See application file for complete search history.

(56) References Cited

U.S. PATENT DOCUMENTS

| 5,629,338 | A | 5/1997 | Okuda et al. |
| 6,294,190 | B1 | 9/2001 | Nakahara et al. |

FOREIGN PATENT DOCUMENTS

| JP | 58-032875 | 2/1983 |
| JP | 01-102022 | 4/1989 |
| JP | 03-219872 | 9/1991 |
| JP | 3-228664 | 10/1991 |
| JP | 03-228664 | 10/1991 |
| JP | 07-061927 | 3/1995 |
| JP | 09-040689 | 2/1997 |
| JP | 2000-226329 | 8/2000 |

OTHER PUBLICATIONS

Nakai et al., "Inhibitory Effects of Oolong Tea Polyphenols on Pancreatic Lipase in Vitro," Agricultural and Food Chemistry, 2005, vol. 53, pp. 4593-4598.

European Search Report issued Dec. 4, 2008, in EP Appln. No. 05743859.0.
Hashimoto et al., "Evaluation of the Anti-oxidative Effect (in vitro) of Tea Polyphenols," Biosci. Biotechnol. Biochem., 67 (2), pp. 396-401, 2003.
Moreno et al., "Inhibitory Effects of Grape Seed Extract on Lipases," Nutrition 19, pp. 876-879, 2003.
Yoshikawa et al., "*Salacia reticulata* and Its Polyphenolic Consitituents with Lipase Inhibitory and Lipolytic Activities Have Mild Antiobesity Effects in Rats," J. Nutri 132:1819-1824 (2002).
Han et al., "Anti-obesity action of oolong tea," International Journal of Obesity (1999) 23, pp. 98-105.
Iwata et al., "Effects of Oolong Tea on Plasma Lipids and Lipoprotein Lipase Activity in Young Women," J. Jpn. Soc. Nutr. Food Sci. 44, (1991), pp. 251-259 (English Translation).
Chin et al., "Clinical Efficacy of Oolong Tea on Anti-Simple Obesity" J. Japanese Soc. Clin. Nutri. (20(1):89-90 (1998) (translation).
International Search Report mailed Aug. 16, 2005 in PCT/JP2005/009666 filed May 26, 2005.
Hashimoto, F., "Tannins and Related Compounds XC. 8-c-Ascorbyl (−)—Epigallocatechin 3-0-Gallate and Novel Dimeric Flavan-3-ols, Oolonghomobisflavans a and b, From Oolongtea. (3)", Chemical & Pharmaceutical Bulletin (1989), vol. 37, No. 12, pp. 3255-3263, p. 3258, left column, compounds.
Hashimoto, F., "Anti-AIDS agents. 24. Evaluation of Tea Polyphenols as Anti-HIV Agents", Bioorganic & Medicinal Chemistry Letters (1996), vol. 6, No. 6, pp. 695-700, p. 697 Oolonghomobisflavans27.
Hashimoto, F., et al. Evaluation of the Anti-Oxidative Effect (in vitro) of Tea Polyphenols, Biosci. Biotechnol. Biochem., 2003, vol. 67, No. 2, pp. 396-401.
Hatano et al., "Flavan Dimers with Lipase Inhibitory Activity from *Cassia nomame*," Phytochemistry, vol. 46, No. 5, 1997, pp. 893-900.
Korean Office Action dated Jul. 27, 2010, issued in Korean Application No. 10-2006-7026819 [in Korean].

*Primary Examiner* — Bernard Dentz
(74) *Attorney, Agent, or Firm* — Drinker Biddle & Reath LLP

(57) ABSTRACT

An object of the present invention is to provide a lipase activity inhibitor that shows high inhibitory activity against pancreatic lipase to suppress the absorption of meal-derived fat and/or which contributes to suppressing and preventing obesity, as well as a food or beverage that has such lipase activity inhibitor incorporated therein. Another object of the invention is to provide a lipase inhibitor of tea origin that suits most consumers' taste and which will not impair the flavor of the food or beverage when incorporated therein. Still another object of the invention is to provide a process for producing said lipase inhibitors. Further object of the invention is to provide antioxidants. To attain these objects, epigallocatechin dimers (oolong homobisflavans) or trimers are incorporated in foods or beverages. As a result, the absorption of meal-derived fat can be suppressed and, in addition, antioxidation effect is obtained. The compounds of the invention can be produced by reacting epigallocatechin gallate with formaldehyde in the presence of an acid.

15 Claims, 5 Drawing Sheets

US 7,989,492 B2

EPIGALLOCATECHIN DIMERS OR TRIMERS HAVING LIPASE INHIBITORY ACTIVITY AND/OR ANTIOXIDANT ACTIVITY

CROSS-REFERENCE TO RELATED APPLICATION

This application is a U.S. National Stage Application of International Application No. PCT/JP2005/009666, filed May 26, 2005, and claims benefit of Japanese application No. 158462-2004 filed May 27, 2004.

TECHNICAL FIELD

This invention relates to epigallocatechin dimers or trimers having lipase inhibitory activity, and foods and beverages that have those dimers or trimers incorporated therein. The invention also relates to epigallocatechin dimers or trimers having antioxidant action, and foods and beverages that have those dimers or trimers incorporated therein. The invention further relates to processes for producing those epigallocatechin dimers and trimers.

BACKGROUND ART

Lipase Inhibitor

With the recent westernization of life style in Japan, the intake of high-fat meals by the Japanese people is ever increasing. According to the 1999 Japanese national nutrition survey, the energy intake of the Japanese people has been decreasing each year but yet their lipid energy ratio has exceeded the normal levels of about 25%. Also, 50-60% of people aged over 60 have been found to have higher-than-normal neutral fat and cholesterol levels (Ministry of Health, Labor and Welfare, "1999 National Nutrition Survey Results Summarized", Rinshou Eiyou 2001, 98(5)577-588).

Obesity is one of the most serious conditions in modern society and is mainly ascribed to excessive intake of lipids. Besides obesity, excessive lipid intake is known to cause the onset of associated diseases including diabetes, hyperlipemia, hypertension, and arteriosclerosis. The only drug that has been approved in Japan for treating obesity is the appetite suppressant Mazindol (registered trademark) but Mazindol has been reported to cause side effects such as dry mouth, constipation, discomfort in the stomach, vomiturition or nausea, etc. (Rinsho Hyoka, 1985, 13(2), pp. 419-459; Rinsho Hyoka, 1985, 13(2), pp. 461-515). Outside Japan, Zenical (registered trademark), a drug having sufficient lipase inhibitory activity to suppress intestinal fat absorption, is on the market for treating obesity, but Zenical has also been reported to cause various side effects such as fatty stools, frequent bowel movements, loose passage, diarrhea, stomachache, etc. (Lancet, 1998, 352, pp. 67-172).

Another way that is known to be effective in preventing obesity is to reduce caloric intake through a diet regimen. However, this approach requires strict nutritional guidance and control and, hence, is difficult to implement in everyday life. Therefore, if body absorption of meal-derived fat could be suppressed in a safe and healthy manner, a practical and effective measure could be offered for treating obesity and associated diseases and promoting health.

Under the circumstances, attention is being drawn to the development of "foods for specified health uses" which have been proven to be safe and effective in humans. Foods for specified health uses that have been sold to date as having the ability to suppress the increase of postprandial serum neutral fat levels include a globin digest that suppresses fat absorption by inhibiting pancreatic lipase (J. Nutr. 1988, 128, pp. 56-60; Journal of Nutritional Science and Vitaminology, 1999, 52(2), pp. 71-77; Kenkou•Eiyou Shokuhin Kenkyu, Japan Health Food & Nutrition Food Association, 2002, 5(3), pp. 131-144), diacyl glycerol having different digestion/absorption characteristics compared to triacyl glycerol (J. Am. Coll. Nutr. 2000, 19(6), pp. 789-796; Clin. Chim. Acta. 2001, 11(2), pp. 109-117), and eicosapentaenoic acid (EPA) and docosahexaenoic acid (DHA) that are purified from fish oil. In order to suppress the absorption of dietary fat using the foods for specified health uses listed above, it is desirable that they are ingested together with meals. However, it is predicted that the foods listed above may affect the flavor of food and beverage to be taken in with the above-listed foods.

Some polyphenols are known to have activity in inhibiting lipase. Among the examples reported so far are tannin derived from plant bark (JP 60-11912 B), tannins or flavonoids and glycosides thereof that are contained in the leguminous plant *Cassia nomame* (JP 8-259557 A), lipid absorption suppressing foods having incorporated therein epigallocatechin gallate and epicathechin gallate that are the main components in green tea (JP 3-228664 A), lipase inhibitors comprising water extracts of green pepper, shimeji mushroom, pumpkin, *Grifola frondosa*, *Sargassum fusiforme* (Harvey) Setchell, green tea or oolong tea (JP 3-219872 A), flavone and flavonols (JP 7-61927 A), hydroxybenzoic acids (gallic acid) (JP 1-102022 A), triterpene compounds and their derivatives (JP 9-40689 A), and antiobesity drugs containing procyanidin of tamarind as an active ingredient (JP 9-291039 A). Also known are lipase inhibitory action of grape seed extract (Nutrition, 2003, 19, (10), pp. 876-879), the lipase inhibitory action of *Salacia oblonga* derived polyphenols and their antiobesity action in rat (J. Nutr., 2002, 132, pp. 1819-1824) and the antiobesity action of oolong tea extract in mouse (Int. J. Obes., 1999, 23, pp. 98-105).

The lipid lowering effect of oolong tea has been reported by many researchers. In one report, subjects were allowed to drink commercial oolong tea in 1330 ml portions daily for six weeks to show a significant drop in blood neutral fat levels (Journal of Nutritional Science and Vitaminology, 1991, 44(4), pp. 251-259) and in another, 102 male and female subjects with simple obesity were orally administered oolong tea (2 g×4/day) for six consecutive weeks and a weight loss of at least 1 kg was observed in 67% of the subjects and, in addition, the subjects showing high blood neutral fat levels exhibited significant improvements after ingesting oolong tea (Journal of The Japanese Society of Clinical Nutrition, 1998, 20(1), pp. 83-90).

Non-patent document 1: Ministry of Health, Labor and Welfare, "1999 National Nutrition Survey Results Summarized", Rinshou Eiyou 2001, 98(5)577-588

Non-patent document 2: Rinsho Hyoka, 1985, 13(2), pp. 419-459

Non-patent document 3: Rinsho Hyoka, 1985, 13(2), pp. 461-515

Non-patent document 4: Lancet, 1998, 352, pp. 67-172

Non-patent document 5: J. Nutr. 1988, 128, pp. 56-60

Non-patent document 6: Journal of Nutritional Science and Vitaminology, 1999, 52(2), pp. 71-77

Non-patent document 7: Kenkou•Eiyou Shokuhin Kenkyu, Japan Health Food & Nutrition Food Association, 2002, 5(3), pp. 131-144

Non-patent document 8: J. Am. Coll. Nutr. 2000, 19(6), pp. 789-796

Non-patent document 9: Clin. Chim. Acta. 2001, 11(2), pp. 876-879

Non-patent document 10: Nutrition, 2003, 19, (10), pp.

Non-patent document 11: J. Nutr., 2002, 132, pp. 1819-1824

Non-patent document 12: Int. J. Obes., 1999, 23, pp. 98-105

Non-patent document 13: Journal of Nutritional Science and Vitaminology, 1991, 44(4), pp. 251-259

Non-patent document 14: Journal of The Japanese Society of Clinical Nutrition, 1998, 20(1), pp. 83-90

Patent document 1: JP 60-11912 B

Patent document 2: JP 8-259557 A

Patent document 3: JP 3-228664 A

Patent document 4: JP 3-219872 A

Patent document 5: JP 7-61927 A

Patent document 6: JP 1-102022 A

Patent document 7: JP 9-40689 A

Patent document 8: JP 9-291039 A

DISCLOSURE OF THE INVENTION

Problems to be Solved by the Invention

The previously reported lipase inhibitors shown above are by no means satisfactory in their efficacy. Even if the extract of a certain plant is shown to be effective, its lipase inhibitory activity is difficult to maintain in a consistent way unless the amount of the active ingredient in the plant extract is clarified, because the extract is of natural origin.

In addition, a lipase inhibitor derived from a plant that does not suit many consumers' taste is most likely to affect the flavor of food or beverage in which it is incorporated. Hence, lipase inhibitors originating from tea that suits many consumers' taste can be promising candidates. On the other hand, if one wants to lower the lipid level with oolong tea that suits many consumers' taste, it has to be drunk in large enough quantities to prove effective but this is not practical in everyday life. Supplying a simple concentrate of oolong tea is not a practical method, either, since it has too much bitterness and pungency and also high caffeine content.

An object, therefore, of the present invention is to provide a lipase activity inhibitor that shows high inhibitory activity against pancreatic lipase to suppress the absorption of meal-derived triglyceride and/or which contributes to suppressing and preventing obesity.

Another object of the present invention is to provide a lipase inhibitor of oolong tea origin that suits many consumers' taste and which will not impair the flavor of the food or beverage when incorporated therein.

Still another object of the present invention is to provide processes for producing said lipase inhibitors.

A further object of the present invention is to provide foods and beverages that have the lipase inhibitors of the invention incorporated therein.

Yet another object of the present invention is to provide an antioxidant that can prevent a variety of conditions resulting from active oxygen including, for example, life-style related diseases such as hypertension, diabetes and hyperlipemia, cardiac diseases such as arteriosclerosis, and aging and cancer.

A still further object of the present invention is to provide a lipase inhibitor and/or an antioxidant, an effective amount of which can be correctly incorporated in foods or beverages.

Means for Solving the Problems

Epigallocathechin Dimers and Trimers

As means for attaining those objects, the present inventors found ingredients in oolong tea that inhibited pancreatic lipase essential to fat absorption. The present inventors evaluated the lipase inhibitory activity of the various polyphenols present in oolong tea and found that an epigallocatechin dimer of the following structure in which epigallocatechin units are polymerized via a methylene group that bridges their chroman rings at 6- or 8-position:

[Formula 1]

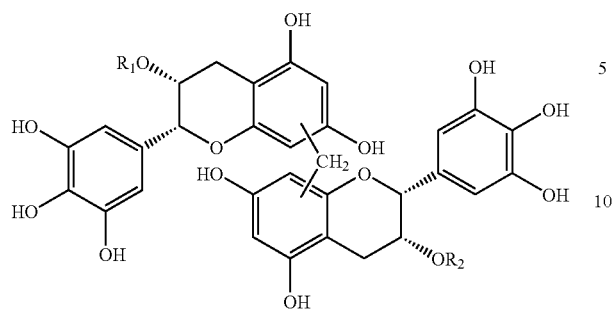

wherein $R_1$ and $R_2$ are each independently H or a galloyl group, had high inhibitory activity.

Preferred dimers of the present invention are compounds represented by the following formulas:

[Formula 2]

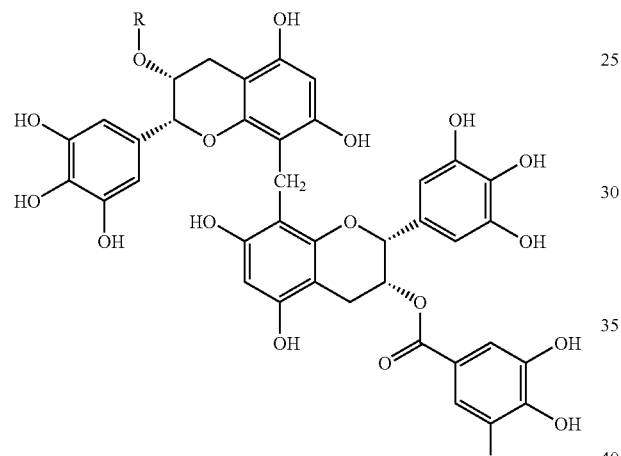

1: R = galloyl
5: R = H

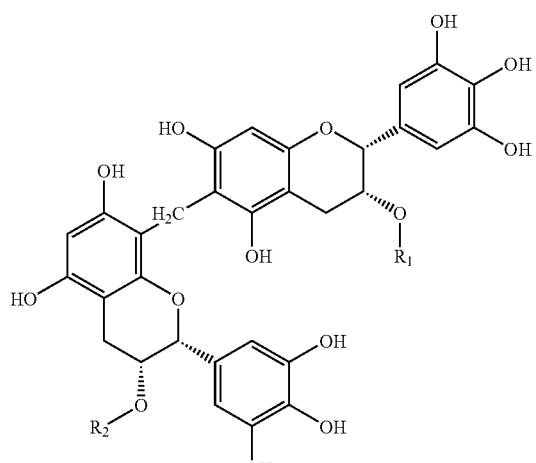

2: $R_1 = R_2 =$ galloyl
6: $R_1 = R_2 =$ H which are oolong homobisflavan A(1), oolong homobisflavan B(2), monodesgalloyl oolong homobisflavan A(5), and didesgalloyl oolong homobisflavan B(6).

According to the present invention, a novel, synthesized epigallocatechin dimer, named oolong homobisflavan C(3):

[Formula 3]

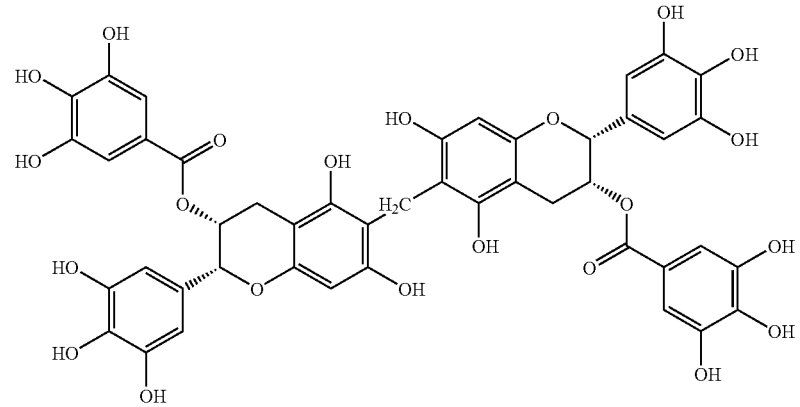

also had high lipase inhibitory activity.

Also according to the present invention, an epigallocatechin trimer of the following structure in which epigallocatechin units are polymerized via methylene groups that bridge their chroman rings at 6- and/or 8-position:

[Formula 4]

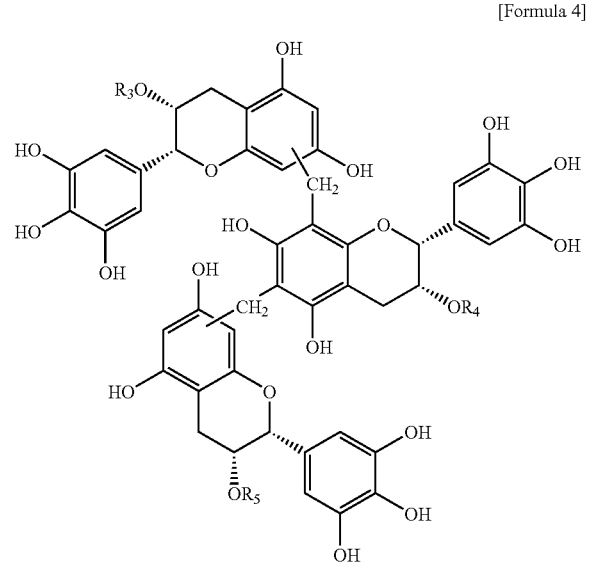

wherein $R_3$, $R_4$ and $R_5$ are each independently H or a galloyl group, also had strong lipase inhibitory activity.

A preferred epigallocatechin trimer is a compound represented by the following formula:

[Formula 5]

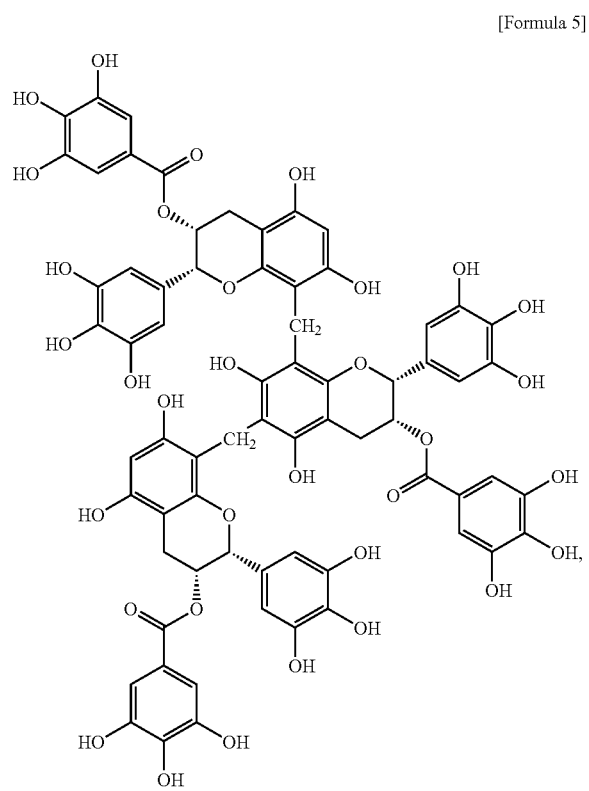

which is named as compound (4).
Production of Epigallocatechin Dimers and Trimers
The epigallocatechin dimers of the present invention can mostly be synthesized or purified for recovery by methods well known to skilled artisans. For example, oolong homobisflavan A(1) and B(2) which are both epigallocatechin dimers can be synthesized by the method described in Chem. Pharm. Bull 37(12), 3255-3563 (1989), whereas monodesgalloyl oolong homobisflavan A(5) and didesgalloyl oolong homobisflavan B(6) can be recovered from tea leaves by the method described in Chem. Pharm. Bull 37(12), 3255-3563 (1989).

The trimers of the present invention are produced by the following procedure. Briefly, they can be produced by a process including the step of reacting flavan-3-ols such as epigallocatechin-3-O-gallate (7) with formaldehyde in a solvent such as methanol or ethanol, preferably methanol, in the presence of an acid such as hydrochloric acid or sulfuric acid, preferably 0.01N hydrochloric acid. The reaction temperature is not limited to any particular value as long as the starting materials and the product are stable but it is preferred to carry out the reaction at room temperature. Alternatively, the trimers can be produced by dissolving flavan-3-ol such as epigallocatechin-3-O-gallate (7) in dimethyl sulfoxide (DMSO) and heating the solution. The heating reaction conditions are not limited in any particular way as long as the starting materials and the product are stable but the reaction is preferably carried out at 150-200° C., more preferably at 180° C., for a period that is preferably between 1 and 30 minutes, more preferably for 15 minutes. The concentration of formaldehyde in the reaction solution is preferably 3-37 w/v %. The resulting product may optionally be esterified, hydrolyzed or otherwise treated to make derived forms.

The methods described above for producing the trimers are also suitable for producing the dimers. For example, as will be later described in Example 3, some dimers including novel homobisflavan C(3) were produced by those methods.
Lipase Inhibitory Activity The compounds of the present invention have lipase inhibitory activity, in particular, pancreatic lipase inhibitory activity.

Lipase inhibitory activity can be measured by any one of the lipase activity assays that are described in the prior applications mentioned in the Background Art. As for inhibitory activity against pancreatic lipase, an oleic ester of fluorescent 4-methylumbelliferone may be used as a substrate to measure the fluorescence from 4-methylumbelliferone that is formed by reaction with the lipase. The amount of a sample that provides 50% inhibition of lipase activity ($IC_{50}$) may be substituted to express lipase inhibitory activity in accordance with the usual method.

As will be shown in Example 1, compounds of the present invention had very low $IC_{50}$ values against pancreatic lipase as compared with the known lipase inhibitor epigallocatechin-3-O-gallate (7).

Therefore, the lipase inhibitors of the present invention can be used in smaller amounts than the heretofore known lipase inhibitors of natural origin and can yet suppress body absorption of meal-derived fat, thereby suppressing the elevation of blood neutral fat and/or preventing obesity. Since the compounds of the present invention are of natural origin, they feature high safety levels and are suitable for daily and/or prolonged intake so that they can exhibit the intended efficacy. In addition, the compounds of the present invention which originate from oolong tea have the advantage of suiting most consumers' taste.

Antioxidant Activity

The present inventors also found that the dimers and trimers of the present invention had the activity of scavenging superoxide anion radicals.

Superoxide anion radicals ($O_2^-$) are a kind of active oxygen formed within the living body, where the radicals not only exhibit sterilizing action but also induce an indiscriminate, strong oxidizing reaction. This effect is believed to cause conditions such as aging and canceration in the living body, typically through the peroxidation of unsaturated fatty acids in cell membranes (see, for example, NANZANDO'S MEDICAL DICTIONARY, 18th ed., p. 329, published Jan. 16, 1998). In addition, a peroxidation reaction of unsaturated fatty acids in food will lead to its deterioration and may even be involved in the emission of off-odor from the food. Therefore, the compounds of the present invention which can scavenge superoxide anion radicals have beneficial characteristics in that they can prevent a variety of conditions resulting from active oxygen including, for example, life-style related diseases such as hypertension, diabetes and hyperlipemia, cardiac diseases such as arteriosclerosis, and aging and cancer.

The superoxide anion radical scavenging activity was measured by the method to be described in Example 5. Briefly, $O_2^-$ was generated by means of hypoxanthine-xanthine oxidase reaction and 5,5-dimethyl-1-pyrrolin-N-oxide was used as a trapping agent to perform measurement by ESR. Measurements were conducted in the presence or absence of compounds of the present invention and the results were expressed as $IC_{50}$ or the amount of a sample that provided 50% suppression of $O_2^-$ generation.

According to Example 5, compounds of the present invention had very low $IC_{50}$ values as compared with compound (7), a known superoxide anion radical scavenger.

Therefore, the compounds of the present invention can be used in smaller amounts than the conventional superoxide anion radical scavengers of natural origin and can yet prevent a variety of conditions resulting from active oxygen including, for example, life-style related diseases such as hypertension, diabetes and hyperlipemia, cardiac diseases such as arteriosclerosis, and aging and cancer. In addition, since the compounds of the present invention are of natural origin, they feature high safety levels and can be ingested over a prolonged period to exhibit the intended efficacy.

Food and Beverage Having Lipase Inhibitor and/or Antioxidant Incorporated Therein The epigallocatechin dimers and/or trimers of the present invention may be incorporated in tea in order to potentiate the polyphenols in it, thereby producing foods and beverages that have not only the action of reducing neutral fat and preventing peroxidation of lipids, aging and obesity, but also the action of preventing a variety of conditions resulting from active oxygen including, for example, life-style related diseases such as hypertension, diabetes and hyperlipemia, cardiac diseases such as arteriosclerosis, and aging and cancer.

Examples of beverages in which the compounds of the present invention may be incorporated include soft drinks, tea beverages, liquid tonics, health drinks, nutrition supply drinks, sports drinks and carbonated drinks (including liquid concentrates and preparatory powders for these beverages), and exemplary foods in which the compounds may be incorporated include gums, candies, jellies, confectioneries in tablet form, health foods, nutrition supply foods, and dietary supplements.

Pharmaceutical Composition Comprising Lipase Inhibitor and/or Antioxidant

The epigallocatechin dimers and/or trimers of the present invention may be used to produce pharmaceuticals that have not only such actions as the one of reducing triglycerides, but also the action of preventing a variety of conditions resulting from active oxygen including, for example, life-style related diseases such as hypertension, diabetes and hyperlipemia, cardiac diseases such as arteriosclerosis, and aging and cancer.

If the compounds of the present invention are to be used as medicines, they are provided in the form of powder, granule, tablet, capsule, solution, injection, dermal solution, emulsion, ointment, etc.

Cosmetics Having Lipase Inhibitor and/or Antioxidant Incorporated Therein

The epigallocatechin dimers and/or trimers of the present invention may be used to produce cosmetics that have various actions including the prevention of lipid peroxidation, retardation of aging, and skin whitening.

Cosmetics in which the compounds of the present invention may be incorporated are facial, skin and hair creams, lotions, gels, mousse, shampoo, rinse, etc.

The compounds of the present invention, which may be synthesized products or purified extraction, may independently be used in foods/beverages, pharmaceutical compositions or cosmetics; alternatively, a mixture comprising more than one compound of the present invention may be added to foods or beverages.

Therefore, if an extract from a starting material such as tea leaves contains more than one compound of the present invention, the extracted mixture may be employed as the lipase inhibitor of the present invention without separating the individual components.

Advantages of the Invention

By adding whichever of oolong tea's polyphenols or epigallocatechin dimers and/or trimers that is a component of the higher lipase inhibitory activity, one can provide beverages that retain the flavor of tea, suit many consumers' taste, and serve the purposes of preventing obesity and promoting health.

The compounds as well as foods and beverages of the present invention also have antioxidant activity and contribute to preventing lipid peroxidation and ageing.

The present invention is described more specifically with reference to the following examples which are by no means intended to limit the scope of the invention.

EXAMPLE 1

Measurement of Lipase Inhibitory Activity

For lipase activity measurement, an oleic ester of fluorescent 4-methylumbelliferone (4-UMO) was used as a substrate and the fluorescence from 4-methylumbelliferone formed by enzyme reaction was measured.

The buffer used in the measurement was 13 mM tris-HCl (pH 8.0) containing 150 mM NaCl and 1.36 mM $CaCl_2$. The substrate 4-UMO (product of Sigma-Aldrich Co.) was prepared as 0.1 M solution in DMSO and then diluted 1.000-fold with the buffer. The lipase subjected to enzyme measurement was swine pancreatic lipase (product of Sigma) that had been diluted to a concentration of 400 U/ml with the buffer.

To start the enzyme reaction, 50 µl of buffered 4-UMO solution and 25 µl of distilled water (or an aqueous solution of sample) were loaded and mixed on a 96-well microplate and 25 µl of the buffered lipase solution was then added. After 30-minute reaction, 100 µl of 0.1 M citrate buffered solution (pH 4.2) was added to quench the reaction and the fluorescence from 4-methylumbelliferone (excitation wavelength: 355 nm; fluorescence wavelength: 460 nm), which was generated by the reaction, was measured with a fluorescence plate reader (Fluoroskan Asent CF: product of Labsystems).

The inhibitory activity of the test sample was determined as its amount that would provide 50% inhibition of lipase activity ($IC_{50}$ in µl) compared to the activity of the control (distilled water).

EXAMPLE 2

Samples of Measurement

Figure 1:
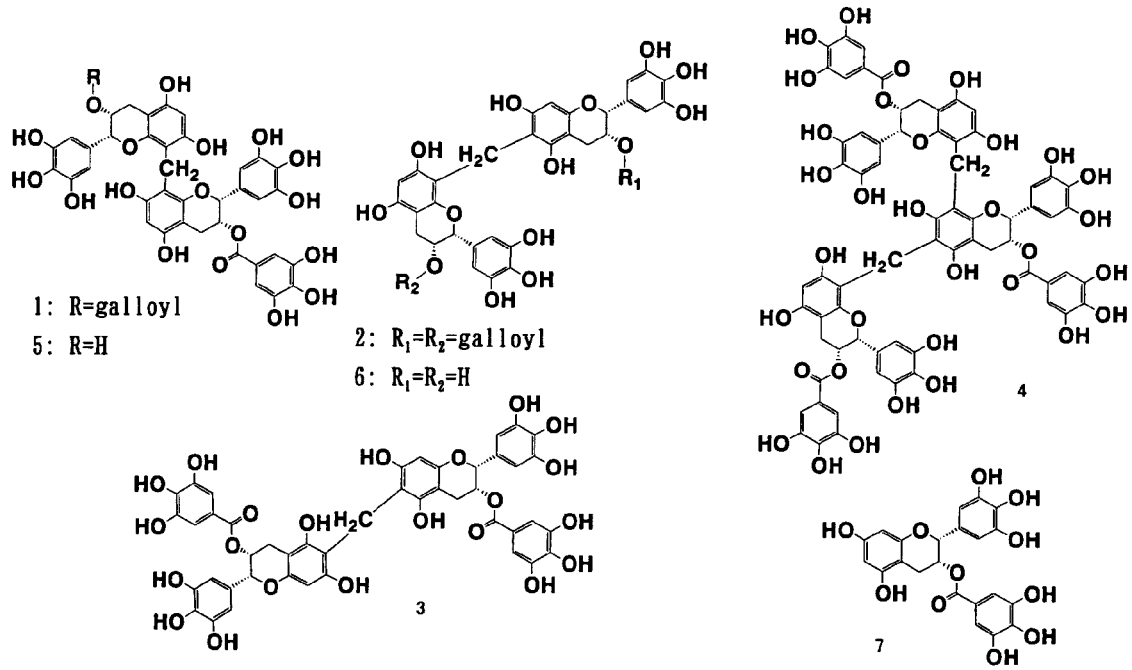
FIG. 1 shows the chemical structural formulas of the samples subjected to the evaluation of their lipase inhibitory activity and antioxidant activity.

Oolong homobisflavan A(1) and oolong homobisflavan B(2) were synthesized in accordance with the article Chem. Pharm. Bull 37(12), 3255-3563 (1989). Monodesgalloyl oolong homobisflavan A(5) and didesgalloyl oolong homobisflavan B(6) were extracted and purified from tea leaves by the method described in Chem. Pharm. Bull 37(12), 3255-3563 (1989). Alternatively, they can be obtained by hydrolysis of oolong homobisflavan A(1) and oolong homobisflavan B(2) with tannase. Novel compounds, oolong homobisflavan C(3) and trimer (4), were synthesized and purified by the methods of Examples 3 and 4 and thereafter determined by instrumental analysis to have the structures shown in FIG. 1. Incidentally, (−)-epigallocatechin-3-O-gallate (EGCG, compound 7) was purchased from Wako Pure Chemical Industries, Ltd.

EXAMPLE 3

Synthesis and Purification of Oolong Homobisflavans (OHBFs)

A. Synthesis:

A hundred milligrams of (−)-epigallocatechin-3-O-gallate (Wako Pure Chemical Industries, Ltd.) was dissolved in 2 ml of methanol containing 0.01N HCl and 18.5% formaldehyde and the solution was stirred at room temperature for 1 hour. After the end of the reaction, the mixture was purified by high-performance liquid chromatography.

B. Conditions of Preparative HPLC:

Column: Develosil C30-UG-5 (2 cmφ×25 cm; Nomura Chemical Co., Ltd.)

Mobile phase: A, 0.1% TFA/$H_2O$; B, 90% $CH_3CN$, 0.1% TFA/$H_2O$; 6 ml/min

Gradient program: B 10%→40% (0-40 min); B 40% iso (40-60 min)

Detection: A 280 nm

Figure 2:
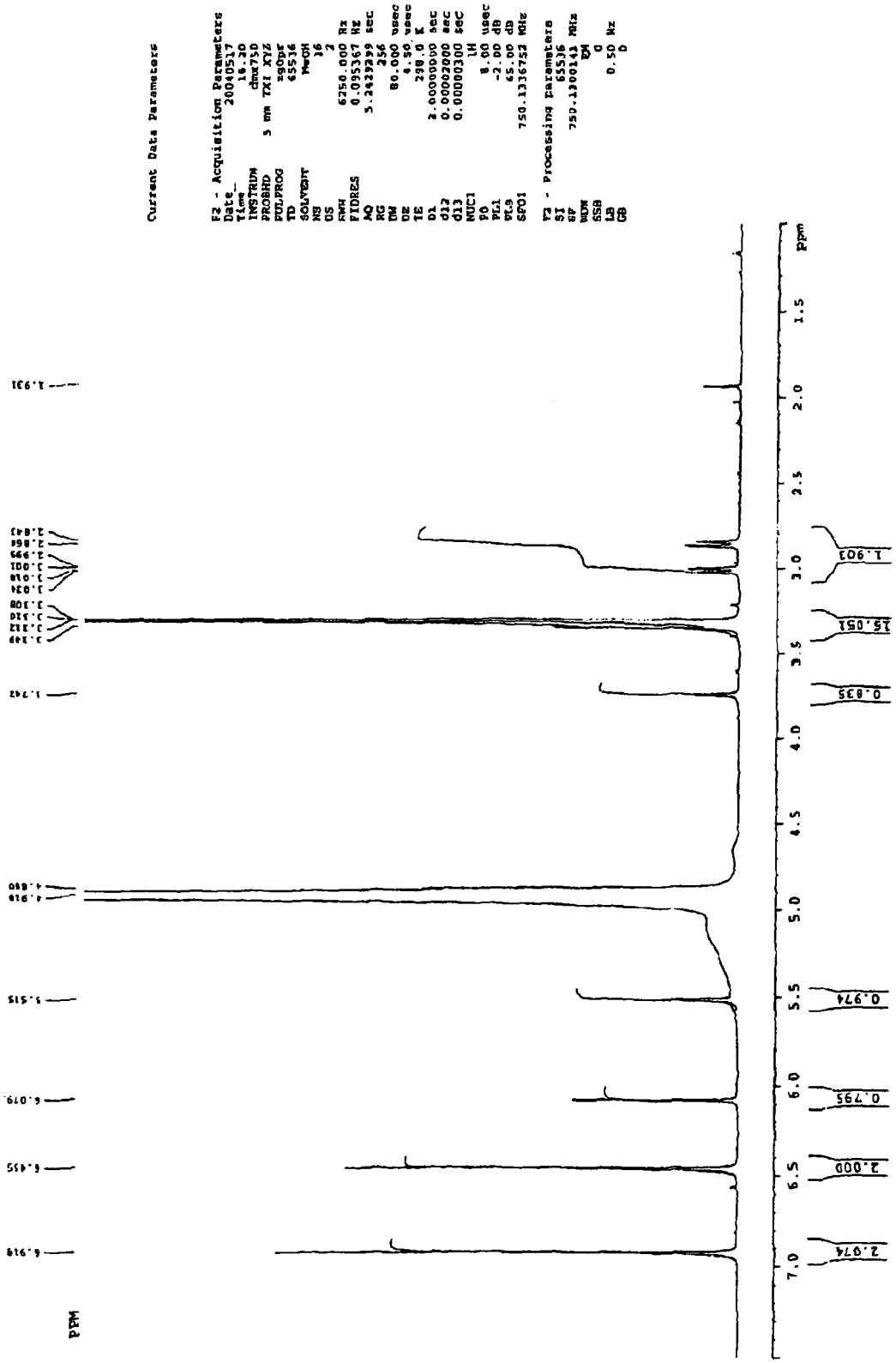
FIG. 2 is a $^1$H-NMR spectrum of oolong homobisflavan C(3)
Figure 3:
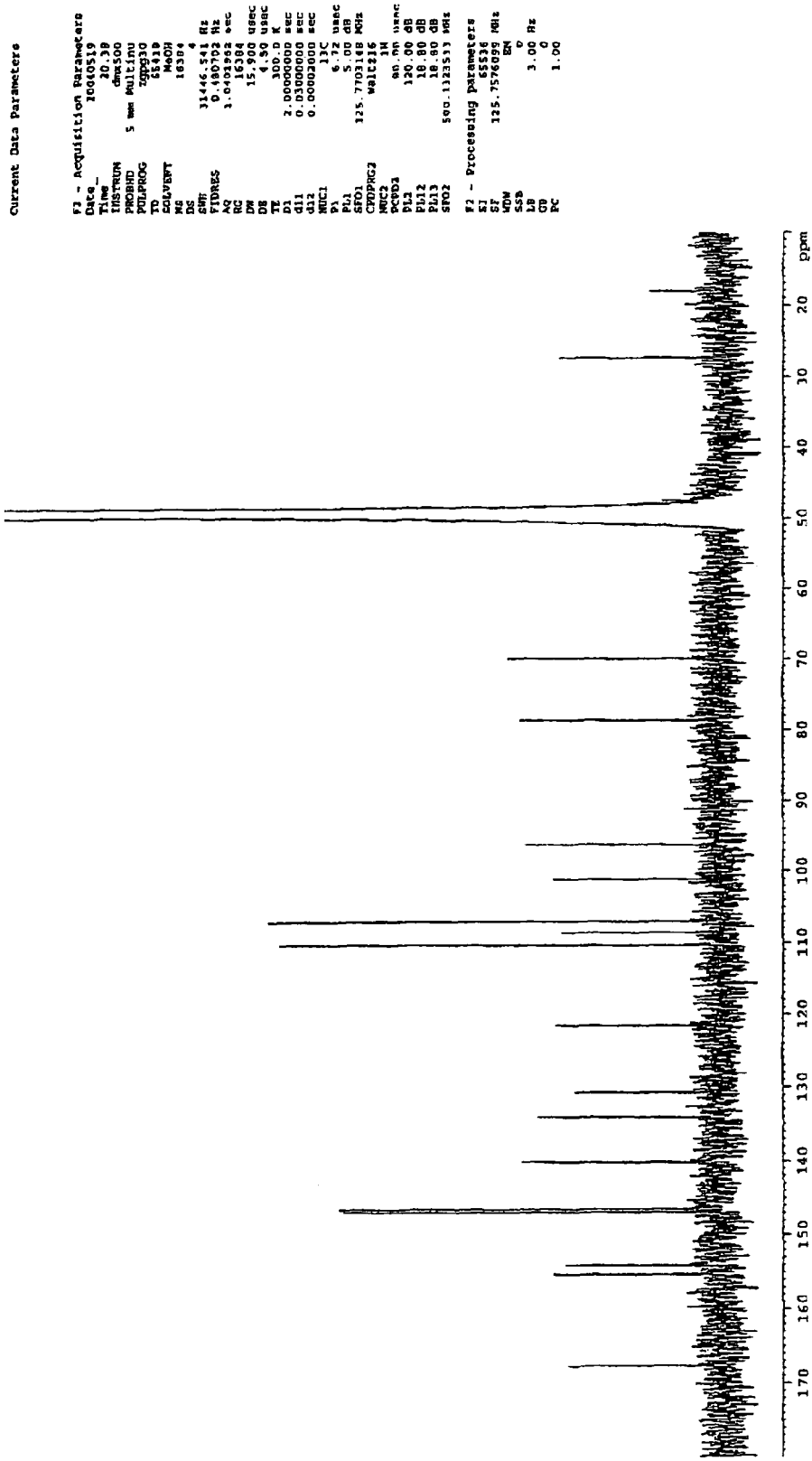
FIG. 3 is a $^{13}$C-NMR spectrum of oolong homobisflavan C(3)
Figure 4:
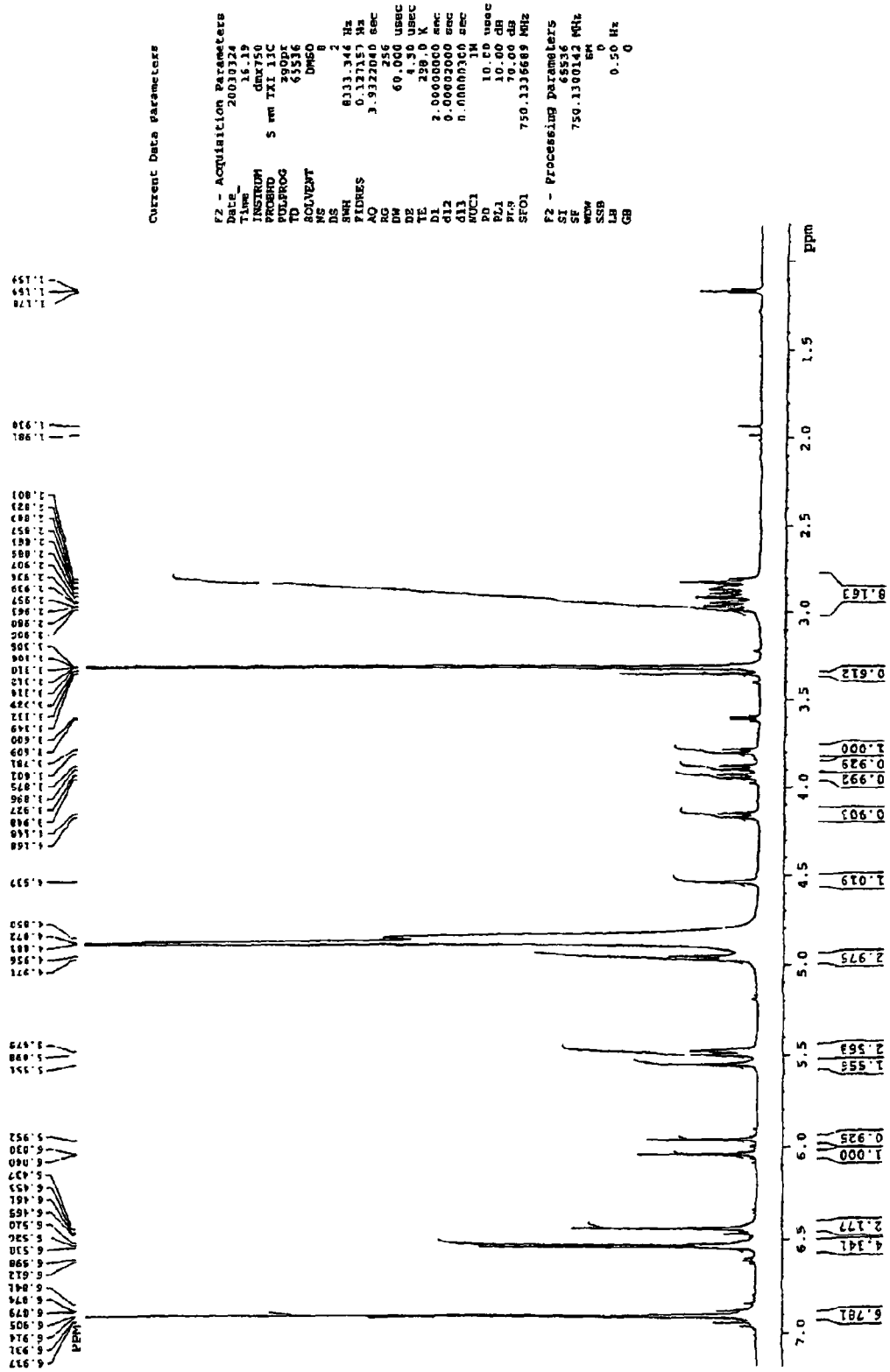
FIG. 4 is a $^1$H-NMR spectrum of trimer (4)
Figure 5:
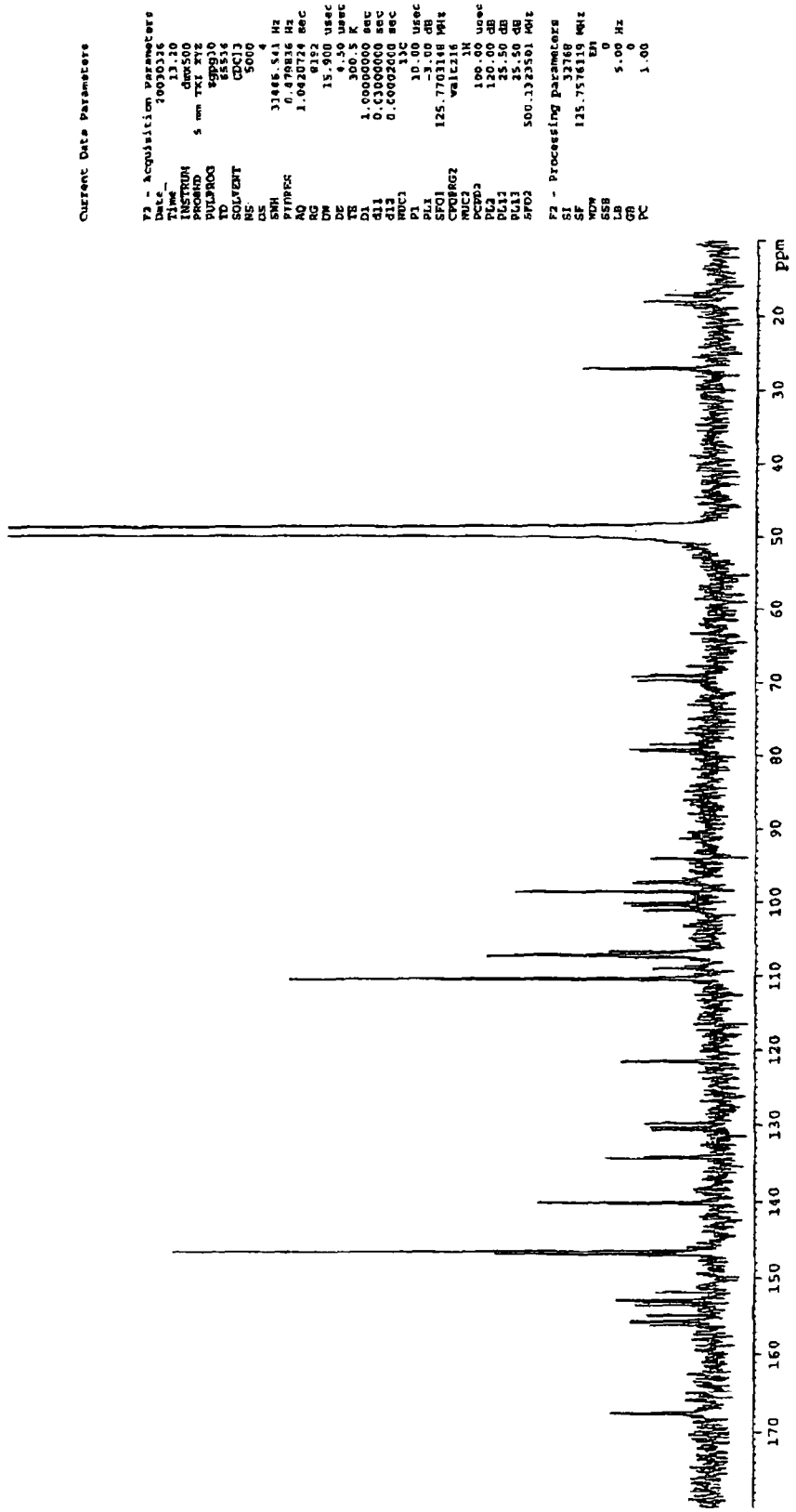
FIG. 5 is a $^{13}$C-NMR spectrum of trimer (4).

Preparative HPLC was performed under the conditions specified above, yielding OHBF-A, OHBF-B, OHBF-C and the trimer in respective amounts of 24.2 mg, 17.2 mg, 5.6 mg, and 13.8 mg. The individual compounds were subjected to MS by micromass Q-TOF in a positive mode, whereupon $[M+H]^+$ ion peaks were detected at m/z 929, 929, 929 and 1399 for OHBF-A, OHBF-B, OHBF-C and the trimer, respectively. The spectral data for OHBF-A and OHBF-B agreed with those shown in Chem. Pharm. Bull 37(12), 3255-3563 (1989), determining that those compounds had the structures represented by formulas 1 and 2 in FIG. 1. As regards OHBF-C and the trimer, NMR measurements for $^1$H-NMR, $^{13}$C-NMR, $^1$H{$^{13}$C}-HSQC, $^1$H{$^{13}$C}-HMBC, TOCSY and DQF-COSY were performed with DMX-750 spectrometer (BRUKER BIOSPIN) to show that those compounds had the structures represented by formulas 3 and 4 in FIG. 1. The $^1$H-NMR and $^{13}$C-NMR spectra of OHBF-C are shown in FIGS. 2 and 3, whereas the $^1$H-NMR and $^{13}$C-NMR spectra of the trimer are shown in FIGS. 4 and 5.

EXAMPLE 4

Lipase Inhibitory Activities of Oolong Homobisflavans and their Trimer

The lipase inhibitory activities of six compounds (dimers of OHBFs and their trimer), as well as epigallocatechin gallate (EGCG) were measured in accordance with Example 1 and the results are shown in Table 1. The chemical structural formulas of the compounds evaluated in Example 4 are listed in FIG. 1.

Dimers of flavan-3-ol having a galloyl group attached to the chroman ring at 3-position via an ester bond, for example, oolong homobisflavan A, B and C, as well as the trimer showed potent lipase inhibitory activity compared with EGCG, so it was suggested that the dimers and trimer in which EGCGs are polymerized would be useful as lipase inhibitors.

Among those compounds, oolong homobisflavan A and B having particularly strong lipase inhibitory activity had been verified to be contained in oolong tea.

TABLE 1

Lipase Inhibitory Activities of Various Polyphenols

| | $IC_{50}$ (µM) |
|---|---|
| Oolong homovisflavan A(1) | 0.049 |
| Oolong homobisflavan B(2) | 0.108 |
| Oolong homobisflavan C(3) | 0.097 |
| Trimer (4) | 0.129 |
| Monodesgalloyl oolong homobisflavan A(5) | 0.271 |
| Didesgalloyl oolong homobisflavan B(6) | 2.083 |
| Epigallocathechin 3-O-gallate (7) | 0.349 |

EXAMPLE 5

Active Oxygen Scavenging Activity

Evaluation was made of the activity for scavenging superoxide anion radicals generated by hipoxanthine-xanthine oxidase reaction, a kind of active oxygen.

Method:

After preparing (1) 2 mM hypoxanthine solution (dissolved in 0.1 M phosphate buffered solution at pH 7.4) and (2) 5.5 mM diethylenetriamine-pentaacetic acid (dissolved in 0.1 M phosphate buffered solution at pH 7.4), 5.0 ml of the solution (1), 3.5 ml of the solution (2), and 1.5 ml of 5,5-dimethyl-1-pyrrolin-N-oxide (DMPO, product of LABO-TECH) were mixed to make reagent 1. A 50-μl portion of reagent 1 was put in a 1.5-ml microtube and incubated at 37° C. for 4 minutes. To the incubated reagent 1, a methanol solution of the sample was added in an amount of 20 μl and then 50 μl of xanthine oxidase (0.4 units/ml) was added, followed by stirring for 10 seconds. The reaction mixture was injected into a hematocrit tube, which was set in an ESR apparatus and sweeping in a magnetic field was started 60 seconds after addition of xanthine oxidase. The conditions of ESR measurement were as follows: Power, 4 mW; C. Field, 335.5 mT, SwWid (±), 5 mT; SwTime, 1 min; ModWid, 0.1 mT; Amp, 160; TimeC, 0.1 sec; Temperature, 20° C.

Among the ESR signals from DMPO-OOH, the signal of the lowest field strength was compared in height to the internal standard $Mn^{2+}$ signal and the ratio (S/M) was assumed to represent the amount of $O_2^-$ and the $O_2^-$ scavenging activity was calculated by the following formula:

$O_2^-$ scavenging activity (%)=100−{100×(S/M in the presence of the sample)/(S/M in the absence of the sample)}

Results:

To evaluate the ability of oolong homobisflavans A, B and C (dimers), as well as the trimer to scavenge superoxide anion radicals ($O_2^-$), their concentrations capable of scavenging 50% $O_2^-$ ($IC_{50}$) were calculated in μM. The control was epigallocatechin gallate (EGCG). Compared to EGCG, the oolong homobisflavans (dimers and trimer) were found to have stronger $O_2^-$ scavenging activity.

TABLE 2

Superoxide Radical Scavenging Activity

| Sample | M.W. | $IC_{50}$ (μM) |
|---|---|---|
| Oolong homobisflavan A(1) | 928 | 7.9 |
| Oolong homobisflavan B(2) | 928 | 8.1 |
| Oolong homobisflavan C(3) | 928 | 6.2 |
| Trimer (4) | 1398 | 10.1 |
| EGCG (7) | 458 | 14.0 |

The invention claimed is:

1. A method for inhibiting lipase activity comprising administering a composition consisting essentially of an epigallocatechin dimer in which epigallocatechin units are poly merized via a methylene group that bridges their chroman rings at 6- or 8-position:

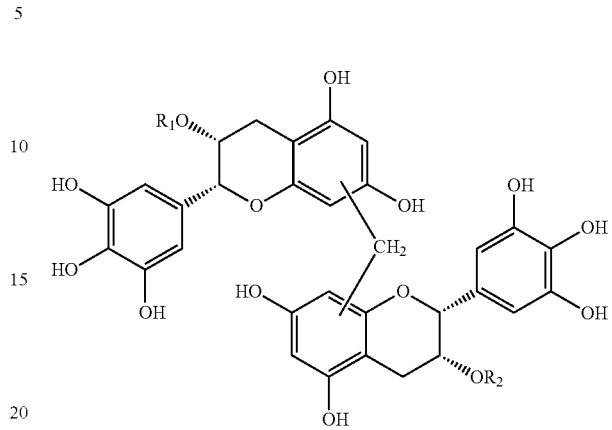

wherein $R_1$ and $R_2$ are each independently H or a galloyl group, and/or an epigallocatechin trimer in which epigallocatechin units are polymerized via methylene groups that bridge their chroman rings at 6- and/or 8-position:

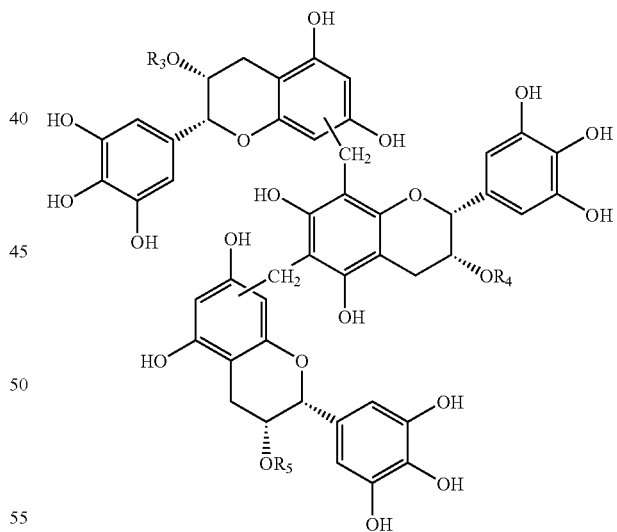

wherein $R_3$, $R_4$ and $R_5$ are each independently H or a galloyl group.

2. The method of claim 1, wherein the epigallocatechin dimer in which epigallocatechin units are polymerized via a methylene group that bridges their chroman rings at 6- or 8-position is oolong homobisflavan A of the formula:

15
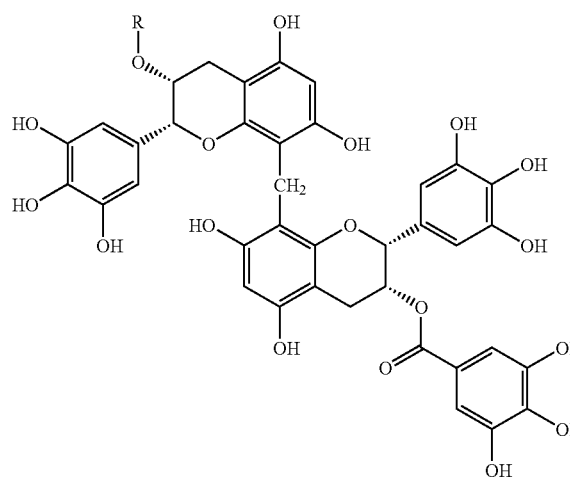
R=galloyl group,
oolong homobisflavan B of the formula:
16
monodesgalloyl oolong homobisflavan A of the formula:
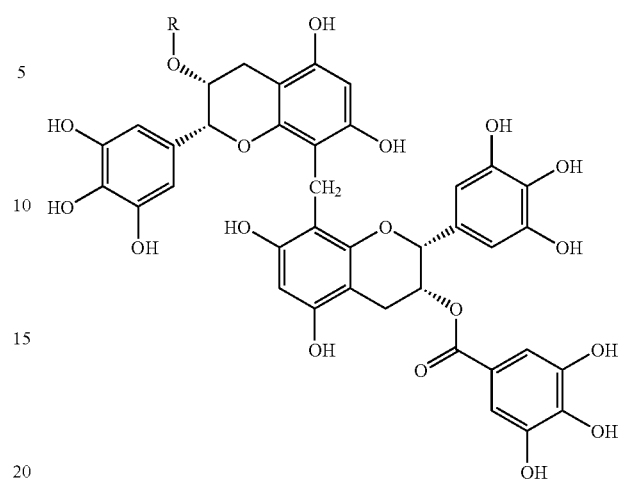
R=H,
didesgalloyl oolong homobisflavan B of the formula:
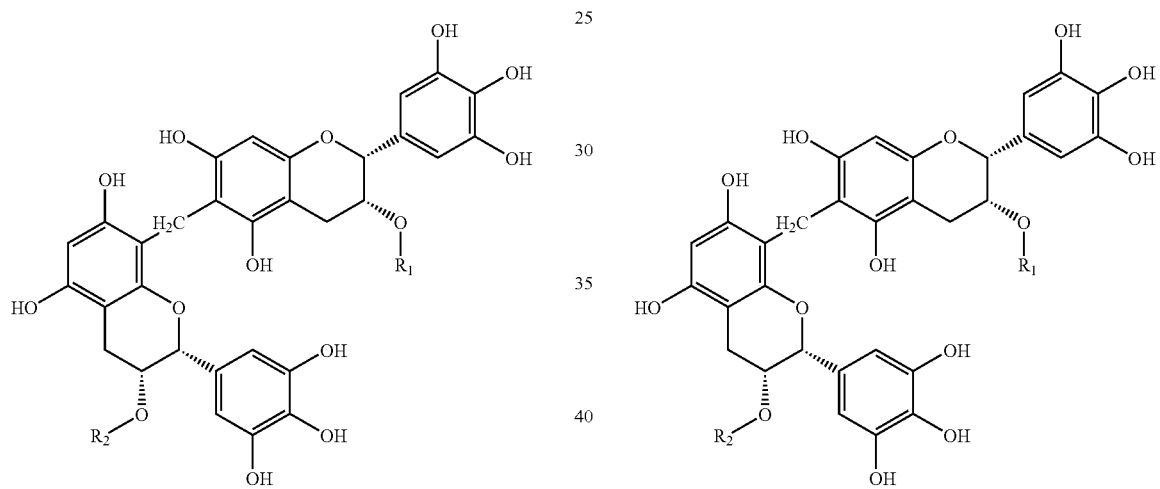
R1=R2=galloyl group,
R1=R2=H,
or oolong homobisflavan c of the formula:
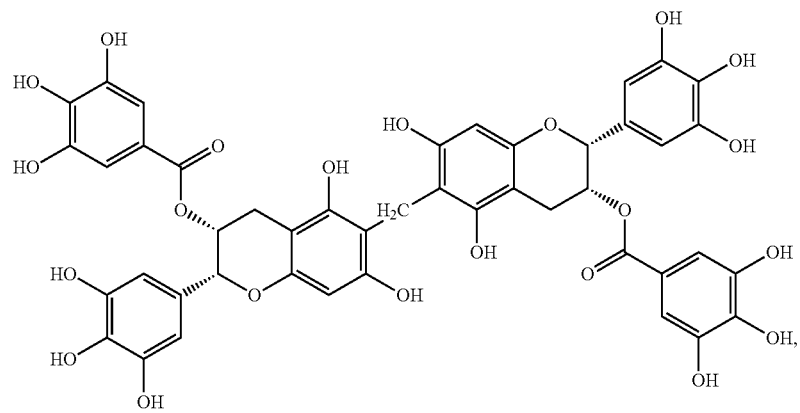

and an epigallocatechin trimer in which epigallocatechin units are polymerized via methylene groups that bridge their chroman rings at 6- and/or 8-positions is a compound of the formula:

catechin units are polymerized via methylene groups that bridge their chroman rings at 6- and/or 8-position:

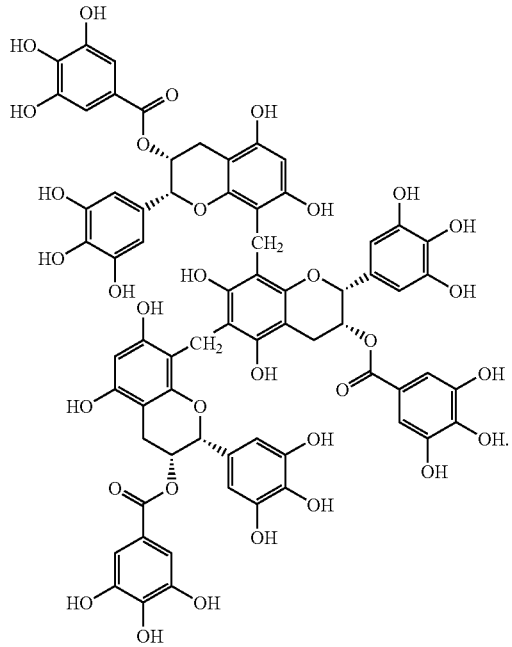

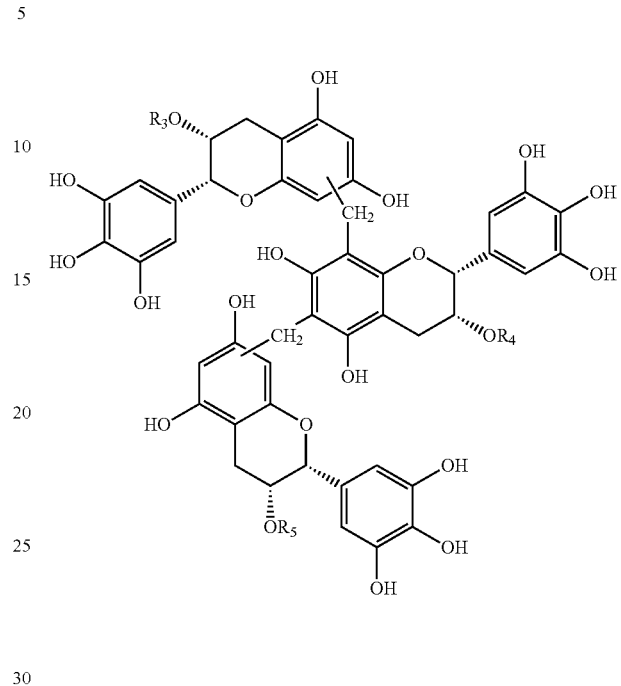

wherein $R_3$, $R_4$ and $R_5$ are each independently H or a galloyl group.

3. The method of claim 1, wherein the composition is a pharmaceutical or food composition.

4. The method of claim 1, wherein the composition is a drink or food.

5. The method of claim 1, wherein the composition is a tea beverage.

6. A method for suppressing body absorption of meal-derived fat, for suppressing the elevation of blood neutral fat, or for suppressing obesity, comprising administering a composition consisting essentially of an epigallocatechin dimer in which epigallocatechin units are polymerized via a methylene group that bridges their chroman rings at 6- or 8-position:

7. The method of claim 6, wherein the epigallocatechin dimer in which epigallocatechin units are polymerized via a methylene group that bridges their chroman rings at 6- or 8-position is oolong homobisflavan A of the formula:

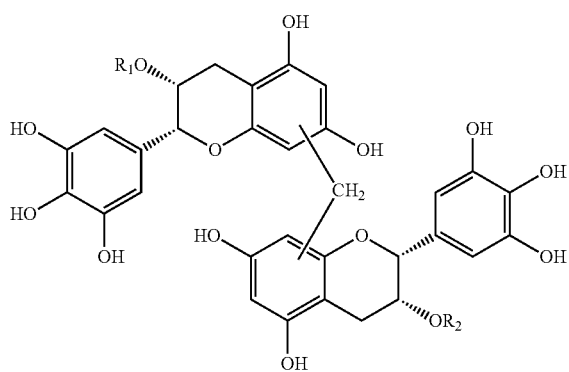

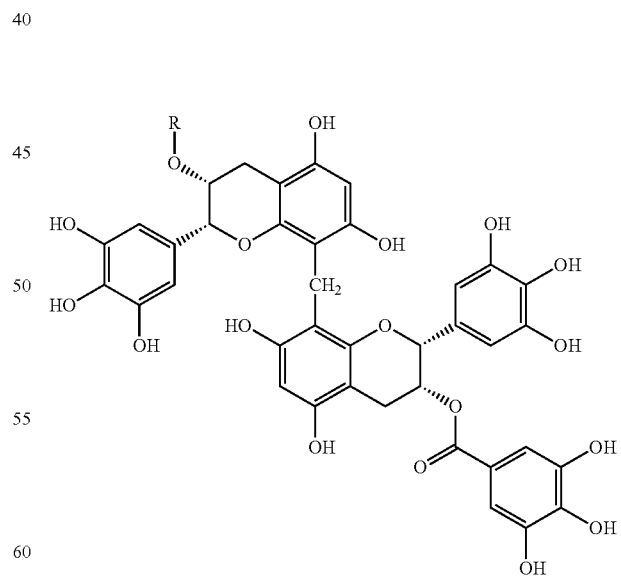

wherein $R_1$ and $R_2$ are each independently H or a galloyl group, and/or an epigallocatechin trimer in which epigallo R=galloyl group, 19
oolong homobisflavan B of the formula:
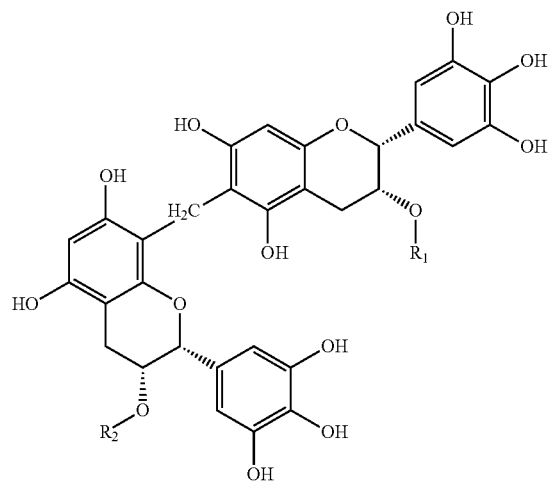
R1=R2=galloyl group,
monodesgalloyl oolong homobisflavan A of the formula:
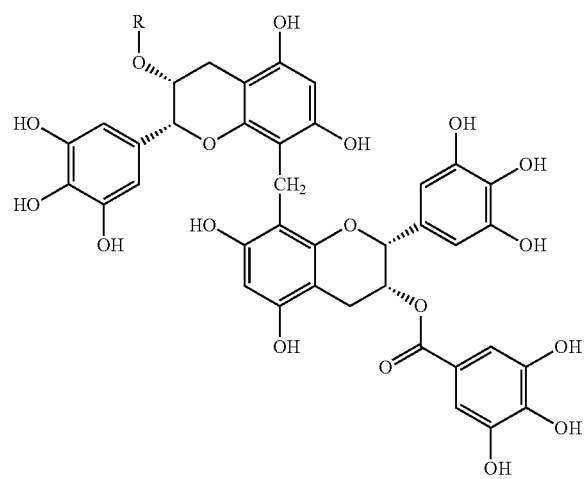
R=H,
20
didesgalloyl oolong homobisflavan B of the formula:
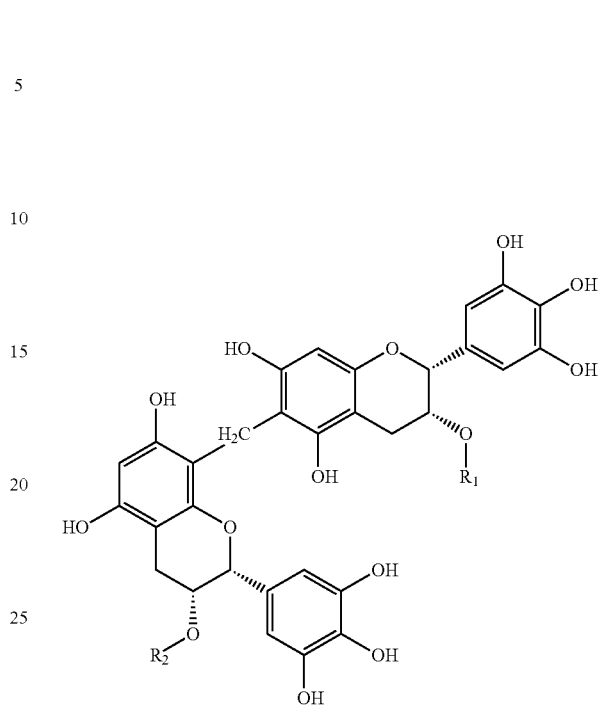
R1=R2=H,
or oolong homobisflavan c of the formula:
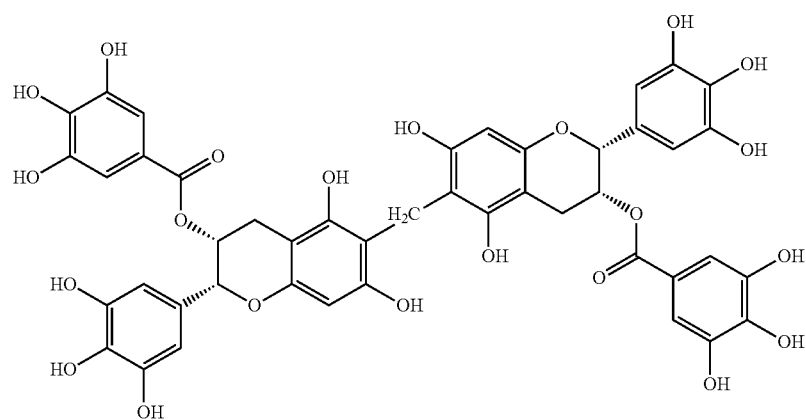

and an epigallocatechin trimer in which epigallocatechin units are polymerized via methylene groups that bridge their chroman rings at 6- and/or 8-positions is a compound of the formula:

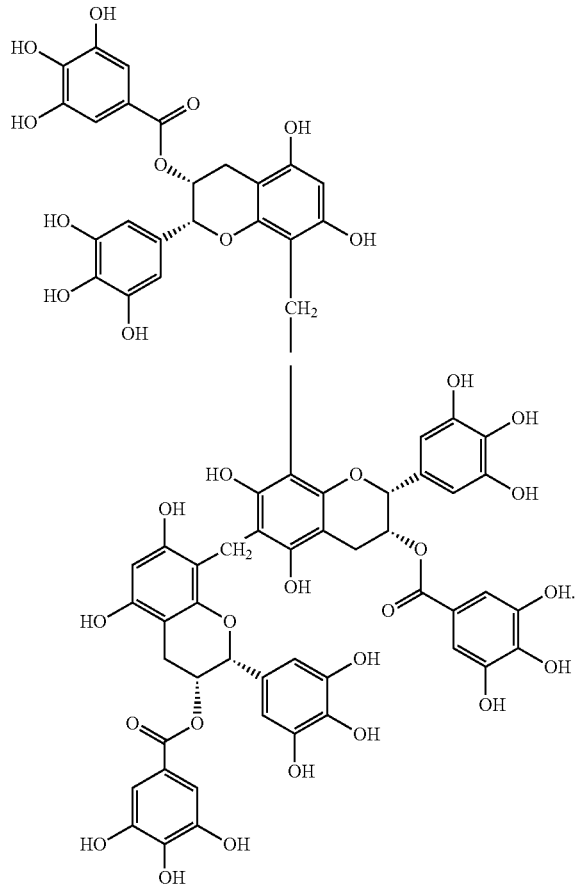

8. A method for inhibiting lipase activity comprising administering to a mammal at least one of the compounds selected from the group consisting of an epigallocatechin dimer in which epigallocatechin units are polymerized via a methylene group that bridges their chroman rings at 6- or 8-position:

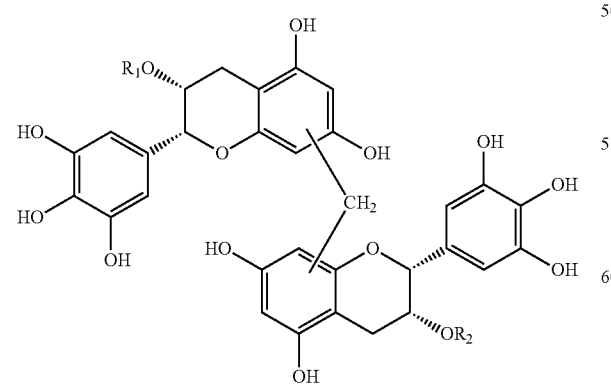

wherein $R_1$ and $R_2$ are each independently H or a galloyl group, and an epigallocatechin trimer in which epigallocatechin units are polymerized via methylene groups that bridge their chroman rings at 6- and/or 8-position:

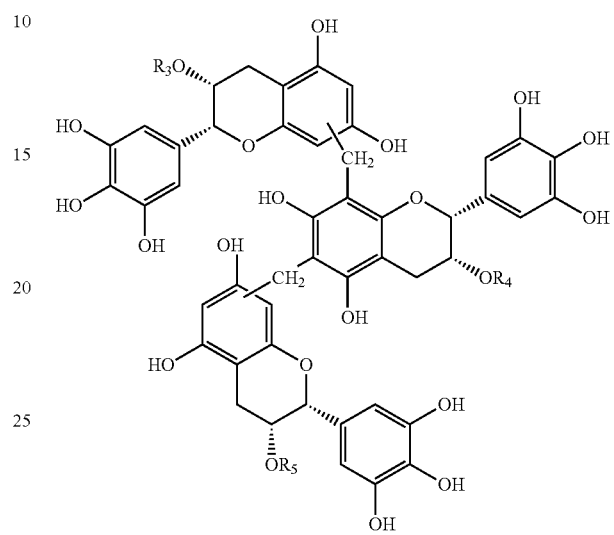

wherein $R_3$, $R_4$ and $R_5$ are each independently H or a galloyl group.

9. The method of claim 8, wherein the epigallocatechin dimer is oolong homobisflavan A of the formula:

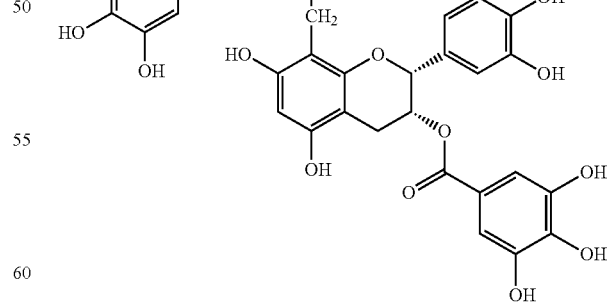

R=galloyl group, 23
oolong homobisflavan B of the formula:
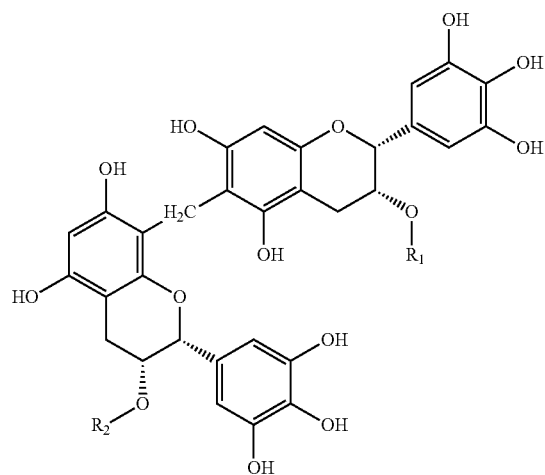
R1=R2=galloyl group,
monodesgalloyl oolong homobisflavan A of the formula:
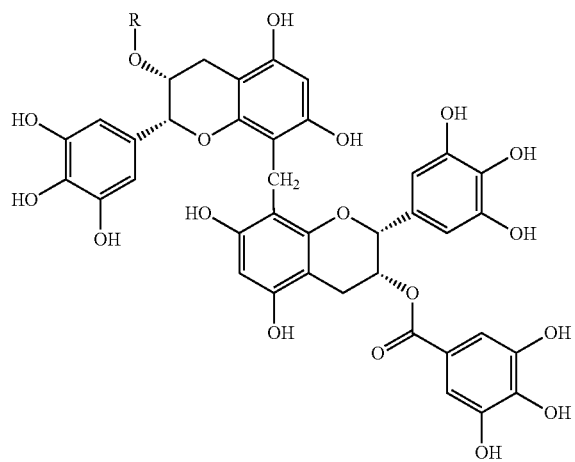
R=H,
24
didesgalloyl oolong homobisflavan B of the formula:
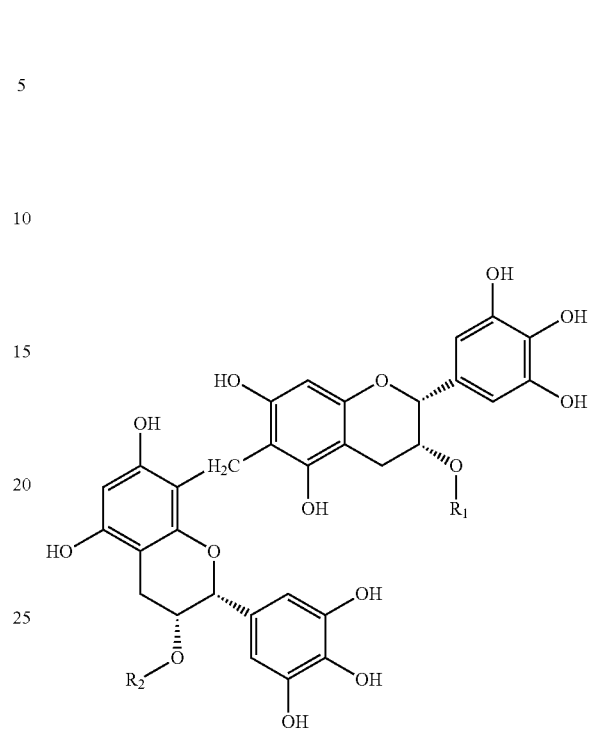
R1=R2=H,
or oolong homobisflavan c of the formula:
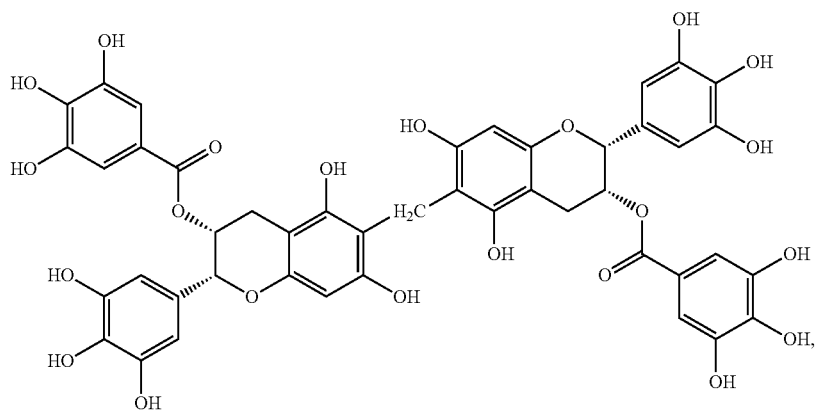

and an epigallocatechin trimer is a compound of the formula:

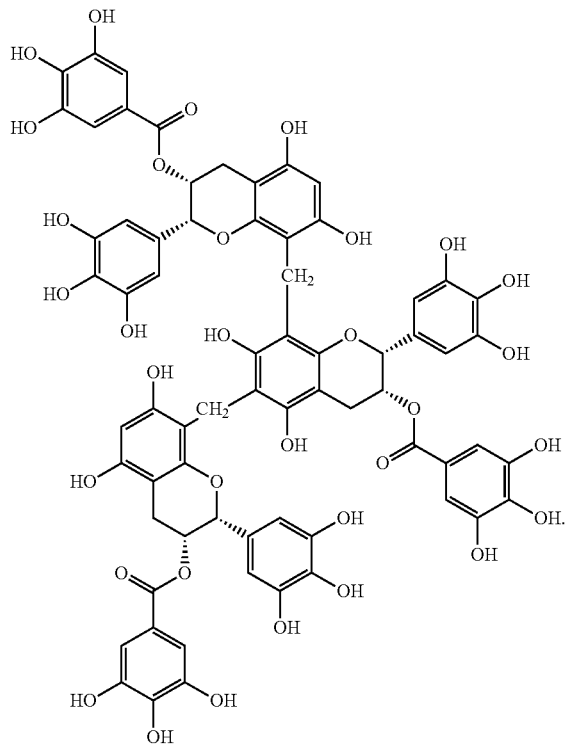

10. The method of claim 8 or 9, wherein at least one of the compounds is included in a food, a beverage, or a pharmaceutical composition.

11. The method of claim 10, wherein the food or beverage is selected from the group consisting of tea drinks, soft drinks, and health foods.

12. A method for suppressing body absorption of meal-derived fat, for suppressing the elevation of blood neutral fat, or for suppressing obesity, comprising administering to a mammal at least one of the compounds selected from the group consisting of an epigallocatechin dimer in which epigallocatechin units are polymerized via a methylene group that bridges their chroman rings at 6- or 8-position:

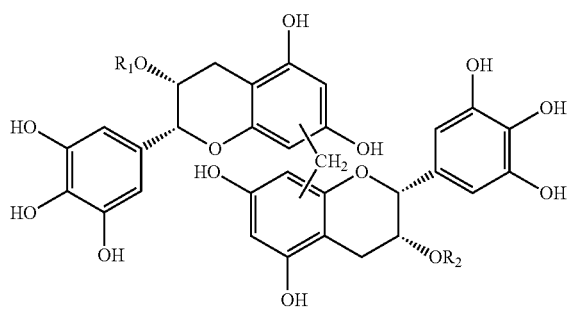

wherein $R_1$ and $R_2$ are each independently H or a galloyl group, and an epigallocatechin trimer in which epigallocatechin units are polymerized via methylene groups that bridge their chroman rings at 6- and/or 8-position:

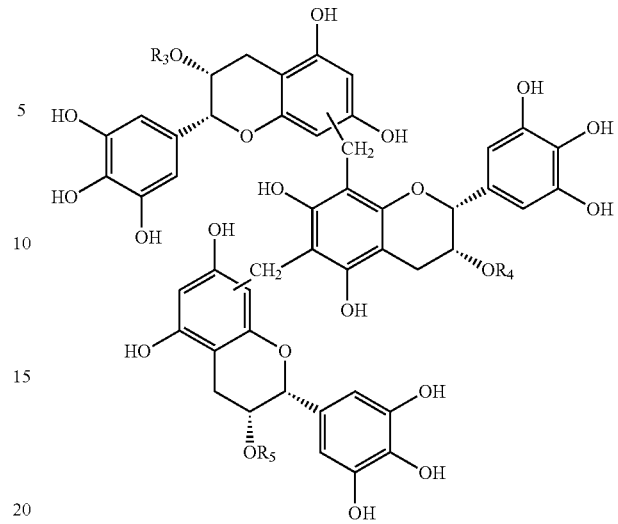

wherein $R_3$, $R_4$ and $R_5$ are each independently H or a galloyl group.

13. The method of claim 12, wherein the epigallocatechin dimer is oolong homobisflavan A of the formula:

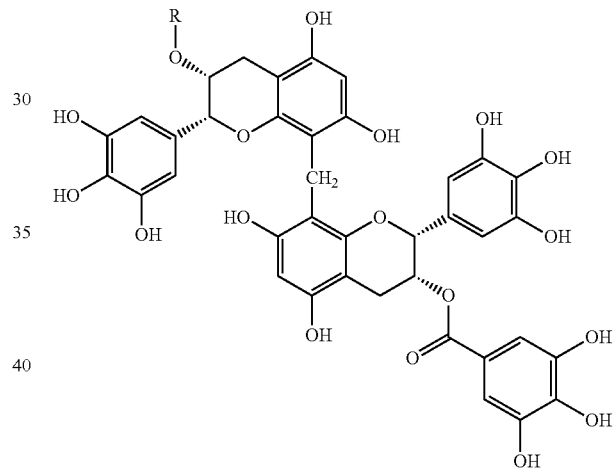

R=galloyl group, oolong homobisflavan B of the formula:

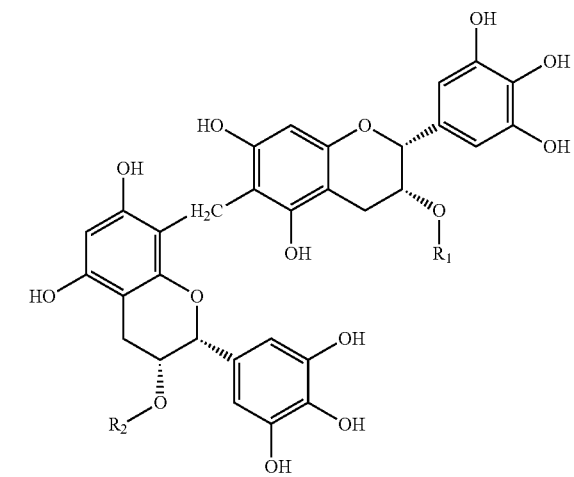

R1=R2=galloyl group, monodesgalloyl oolong homobisflavan A of the formula:
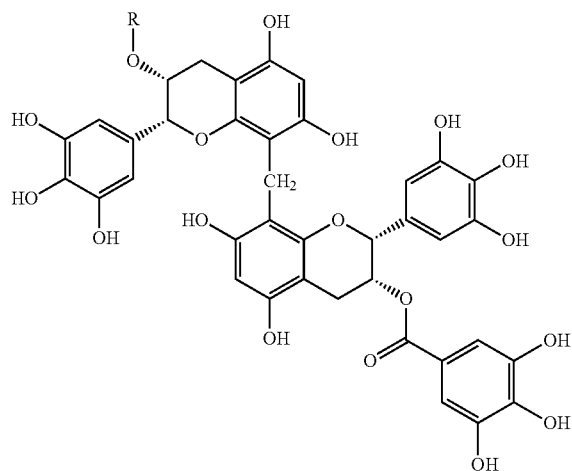
R=H,
didesgalloyl oolong homobisflavan B of the formula:
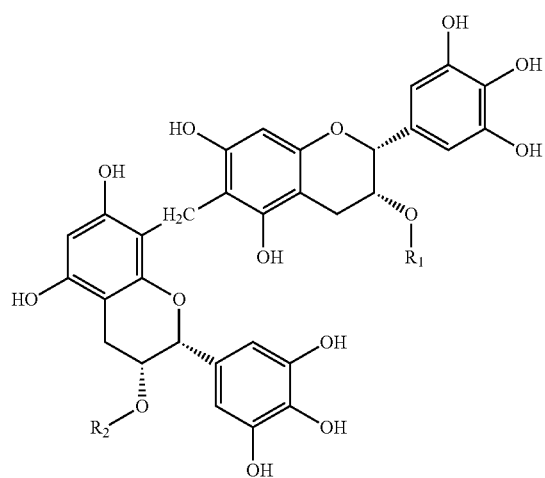
R1=R2=H,
or oolong homobisflavan c of the formula:
and an epigallocatechin trimer is a compound of the formula:
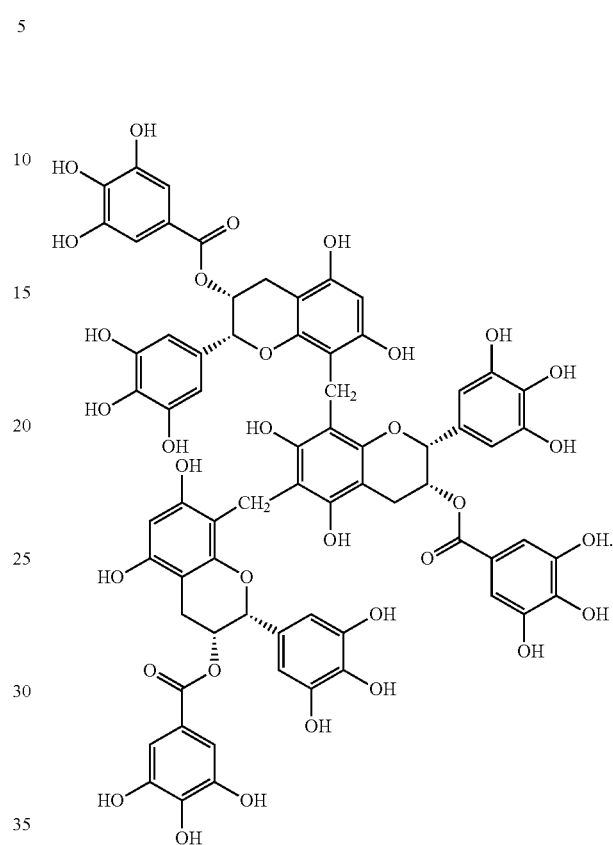
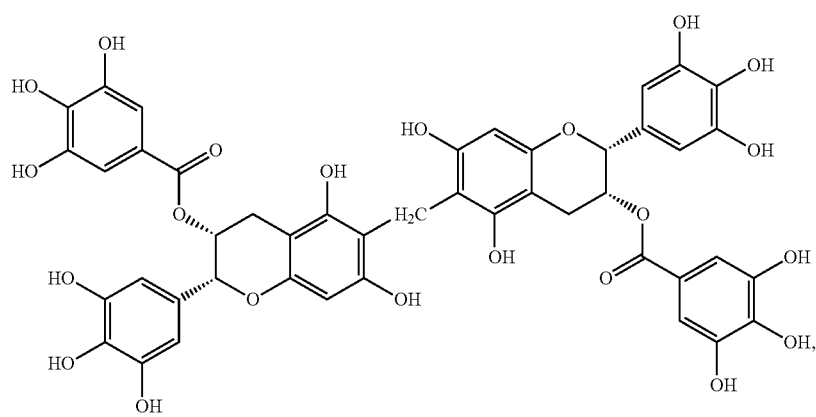

14. The method of claim 12 or 13, wherein at least one of the compounds is included in a food, a beverage, or a pharmaceutical composition.

15. The method of claim 14, wherein the food or beverage is selected from the group consisting of tea drinks, soft drinks, and health foods.

* * * * *